United States Patent [19]
Ruettimann et al.

[11] Patent Number: 5,696,290
[45] Date of Patent: Dec. 9, 1997

[54] SYNTHESIS OF PENTA-SUBSTITUTED GUANIDINES

[75] Inventors: Kenneth W. Ruettimann, East Longmeadow, Mass.; William D. McGhee, Creve Coeur; A. John Solodar, University City, both of Mo.

[73] Assignee: Monsanto Company, St. Louis, Mo.

[21] Appl. No.: 304,322

[22] Filed: Sep. 12, 1994

[51] Int. Cl.$^6$ .................................. C07C 277/08
[52] U.S. Cl. .................... 564/238; 564/230; 564/237; 564/239; 564/240
[58] Field of Search .................... 564/230, 237, 564/238, 239, 240

[56] References Cited

U.S. PATENT DOCUMENTS

| | | | |
|---|---|---|---|
| B 553,652 | 3/1976 | Cherkofsky | 260/565 |
| 4,358,613 | 11/1982 | Mark | 564/238 |
| 4,471,137 | 9/1984 | Barton et al. | 564/240 |
| 5,189,205 | 2/1993 | McGhee | 560/345 |

FOREIGN PATENT DOCUMENTS

| | | |
|---|---|---|
| 10 64 051 | 4/1958 | Germany. |
| 11 70 931 | 5/1964 | Germany. |

OTHER PUBLICATIONS

Broderick and Broderick in Chem. Ber. 1961, 94, 2278.
J. Chem., Soc. Perkin Trans. I 1982, pp. 2085–2090.
Advanced Organic Chemistry (3rd Edition, 1985) p. 376.
Chem. Soc. Rev., vol. 4, 231–250 (1975).
Methoden Der Organischen Chemie, 4th Edition by Houben–Weyl, Vo. 8, p. 157 (1952 or 1954) and p. 151.
Methoden Der Organischen Chemie, Houben–Weyl, vol. E–4, (1983), pp. 340 and 343.
J. Chem. Soc., Chem. Commun, 1994, 957.
Journal of Organic Chemistry, vol. 51, No. 10, May 16, 1986 Easton US, 1719–1723. W. Lwowski et al., "The Photolysis of Carbamoyl Azides in the Presence of Carbodiimides".
Chemical Abstracts, vol. 97, No. 21, 22 Nov. 1982. Columbia, Ohio, US; abstract No. 182236, Ogonor, J.I., p. 812.
Chemische Berichte, vol. 97, No. 5, 1964 Weinheim De, pp. 1232–1245, H. Eilingsfeld et al., "Synthese and Reaktionen von Chlorformamidiniumchloriden"; see pp. 1237–1238.
Chemical Abstracts, vol. 119, No. 15, 11 Oct. 1993, Columbus, Ohio, U.S.; abstract No. 159904, Wu, Zhiguang et al. p. 889.
Chemical Society Reviews, vol. 4, No. 2, 1975, pp. 231–250, D.P. N Satchell "Acylation by Ketens and Isocyanates. A Mechanistic Comparison".

*Primary Examiner*—Peter O'Sullivan
*Attorney, Agent, or Firm*—Fitzpatrick, Cella, Harper & Scinto

[57] ABSTRACT

The present invention is the novel synthesis of sterically hindered penta-substituted guanidines by a process in which (1a) an isocyanate is reacted first with a di-substituted amine or (1b) a urea is reacted with two moles of a mono-substituted amine to form a tri-substituted urea followed by (2) treatment of the tri-substituted urea with an activating agent before reacting with a second di-substituted amine in the presence of a base.

10 Claims, No Drawings

SYNTHESIS OF PENTA-SUBSTITUTED GUANIDINES

BACKGROUND OF THE INVENTION

The present invention is the novel synthesis of sterically hindered penta-substituted guanidines by a process in which an isocyanate is reacted first with a di-substituted amine or a urea is reacted with two moles of a mono-substituted amine then di-substituted amine to form a tri-substituted urea followed by treatment with an activating agent before reacting with a second di-substituted amine in the presence of a base. Although the invention process may be carried out in a one pot process the tri-substituted urea may be isolated.

Penta-substituted guanidines are important for use as agricultural chemicals and pharmaceutical agents or as intermediates in the preparation of agents for such uses. These agents include urethanes, polyurethanes, and blocked isocyanates.

The method shown by Broderick and Broderick in Chem. Ber. 1961, 94, 2278 is the most widely used method for preparing substituted guanidines by reacting tetra-substituted ureas with a mono-substituted amine in the presence of a phosphoroxychloride.

Subsequently, Barton et al in J. Chem. Soc. Perkin Trans. I 1982, pp 2085–2090, Mark in U.S. Pat. No. 4,358,613, and Barton et al in U.S. Pat. No. 4,471,137 for highly sterically hindered guanidines show various processes for the preparation of penta-substituted guanidines. However, these particularly show a tetra-substituted urea intermediate and require phosgene an activating agent.

The exchange of amines with ureas to make other ureas is well-known. March's book, *Advanced Organic Chemistry*, (3rd edition, 1985), page 376, provides a number of such exchanges which are used to make mono- and di- substituted ureas. However, no mention of the urea exchange method are given to make tri-substituted ureas.

Examples from Organic Syntheses cited by March are as follows:

PhNH$_2$+NH$_2$CONH$_2$→PhNHCONH$_2$+PhNHCONHPh

MeNH$_2$+NH2CONH$_2$→MeNHCONH$_2$

EtOPhNH$_2$+NH$_2$CONH$_2$→EtOPhNHCONH$_2$

Me$_2$NH+NH$_2$CONH$_2$→Me$_2$NHCONH$_2$

March (page 802) also cites "Chem Soc. Rev." vol. 4, 231–250 (1975) for the synthesis of mono-, di- and tri-substituted ureas by conventional chemistry showing the reaction of isocyanate plus amines. Such reactions may be shown as follows:

RN=C=O+R"R'NH→RNHC(O)NR'R"

The compendium *Methoden Der Organischen Chemie*, 4th edition by Houben-Weyl, Vol 8, p 157 (1952 or 1954) shows the synthesis of tri-substituted ureas, but only via a reaction of isocyanates with dialkyl amines. This same reference does discuss the preparation of ureas by urea exchange (p 151), but only mono and di-substituted ureas are reported. A mechanistic picture of the exchange reaction is also shown on page 151.

A supplement to *Methoden Der Orgsnischen Chemie*, Houben-Weyl, Vol E-4, p 340 (1983) describes a process for making tri-substituted ureas via reaction of carbamoyl chlorides with secondary amines which is shown as follows:

RNHC(O)Cl+R'R"NH→RNHC(O)NR'R"

In the same supplement at page 343 a preparation of tri-alkyl ureas via urea exchange is shown as follows:

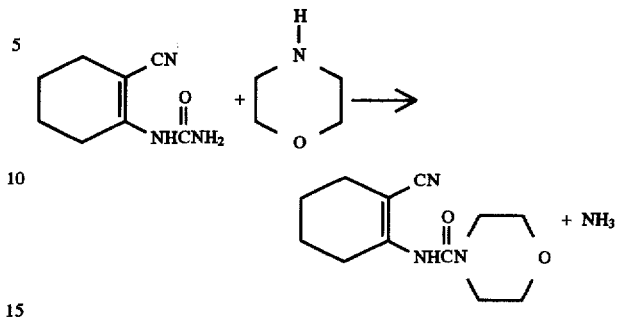

Although this reaction in xylene at a reflux temperature provides an 80% yield it is limited because the starting urea in losing the cyclohexenyl group produces a morpholino urea resulting in a byproduct which is wasted material. This is shown as follows:

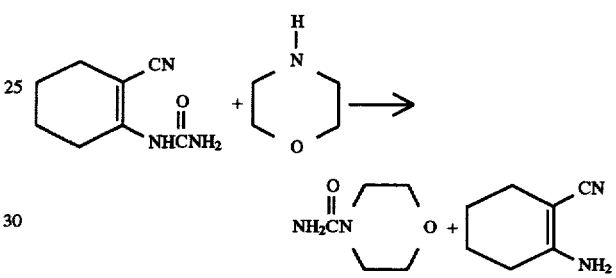

Houben-Weyl volume E-4 also show an analogous urea synthesis in a reaction which contains two very labile diazole groups, i.e. easily removed diazole groups. However, this doesn't provide a conventional tri-substituted urea. This reaction is shown as follows:

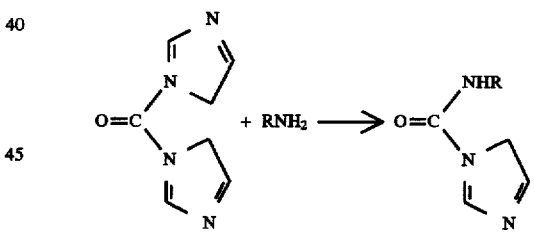

SUMMARY OF THE INVENTION

The present invention is a process for the preparation of penta-substituted guanidines, particularly more hindered penta-substituted guanidines. The invention process provides an efficient and economical, high yield process for the preparation from inexpensive, readily available starting materials.

According to the invention, a process for preparing penta-substituted guanidines is provided which comprises reacting a tri-substituted urea with a di-substituted amine in the presence of an aprotic solvent, a base, and an activating agent which is an electrophilic or oxophilic agent under conditions of time and temperature sufficient to produce the corresponding guanidines; the tri-substituted urea being prepared by contacting equimolar amounts of a substituted isocyanate and a di-substituted amine also in the presence of an aprotic solvent and under conditions of time and temperature sufficient to produce the corresponding tri-substituted ureas, or treating a urea with a primary amine to produce the corresponding tri-substituted ureas.

In one embodiment the tri-substituted urea is recovered prior to reacting the tri-substituted urea with a second di-substituted mine in the presence of an activating agent in the presence of an aprotic organic solvent and a base.

DETAILED DESCRIPTION OF THE INVENTION

Examples of isocyanates useful for the process of the invention include, but are not limited to, alkyl isocyanate, alkenyl isocyanate, cycloalkyl isocyanate, cycloalkenyl isocyanate, aryl isocyanate, aralkyl isocyanate, aralkenyl isocyanate, alkenaryl isocyanate and alkaryl isocyanate, wherein alk represents a carbon chain of from one to twenty carbons, such as cyclohexyl isocyanate, octyl isocyanate, isopropyl isocyanate.

Examples of primary amines which can be employed in the process of the invention include but are not limited to amines such as those that include a substituent which correspond to substituents of the guanidines prepared in the process of the present invention, i.e., alkyl, alkenyl, cycloalkyl, cycloalkenyl, aryl, aralkyl, aralkenyl, alkenaryl and alkaryl wherein each of alkyl, alkenyl, cycloalkyl, cycloalkenyl, aryl, aralkyl, aralkenyl, alkenaryl and alkaryl is of from one to twenty -two carbon atoms, such as cyclohexyl, octyl, isopropyl, ethyl. These are, for example cyclohexyl amine, octyl amine, aniline, methyl amine, ethyl, amine, n-propyl amine, isopropyl amine, n-butyl amine, isobutyl amine, t-butyl amine, n-pentyl amine, isopentyl amine, n-hexyl amine, n-octyl amine, benzyl amine.

Examples of di-substituted amines are in like manner amines such as include two substituents wherein the substituents are independently selected from but not limited to a substituent corresponding to those substituents of the guanidines prepared in the invention process.

Particularly the invention relates to a process for preparing a penta-substituted guanidine of the formula (I)

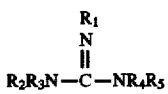

wherein $R_1$, $R_2$, $R_3$, $R_4$ and $R_5$ are the same or different and are selected from the group consisting of alkyl, cycloalkyl, aryl, alkaryl, aralkyl, alkenyl, cycloalkenyl, alkenaryl and aralkenyl;

which comprises treating a compound of the formula (II)

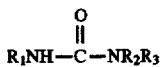

with a compound of the formula (III)

in a aprotic organic solvent in the presence of an activating agent (such as an electrophile or oxophile described in U.S. Pat. No. 5,189,205 which is incorporated herein by reference therefor) and alternatively 1) in the presence of a base such that the pH of the reaction mixture is about the same as or higher than the product of the formula I or 2) followed by addition of a base; and optionally, wherein the compound of the formula II is prepared by a process which comprises (1) treating a compound of the formula (IV)

with a compound of the formula (V)

wherein $R_1$, $R_2$ and $R_3$ are as defined above;
or
(2) treating a compound of the formula (VI)

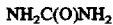

with a compound of the formula (VII)

and then with a compound of the formula (V)

or
(2) treating a compound of the formula (VI)

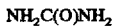

with a compound of the formula (V)

and then with a compound of the formula (VII)

to obtain a compound of the formula II.

Of these the preparation of the compound of the formula IV may be carried out in a manner analogous to that shown by Waldman et al in the *J. Chem. Soc., Chem. Commun.*, 1994, 957.

Applicable solvents for use in the process of the invention are aprotic organic solvents. While both polar and hoaxpolar aprotic organic solvents, as well as mixtures thereof, may be used, it is currently preferred to use non-polar aprotic organic solvents due to reduced occurrence of side reactions. As utilized herein, the phrase polar aprotic organic solvent means an aprotic organic solvent having a dielectric constant measured at 25° C. of greater than about 10 as reported in Reichardt, C., Solvents and Solvent Effects in Organic Chemistry, 2nd ed., VCH Verlagsgesellschaft, Weinheim, (1988), Table A-1. Other methods for determining dielectric constant greater than that of tetrahydrofuran utilizing any of such methods.

Examples of non-polar aprotic organic solvents which can be employed in the process of the invention include dichloromethane, toluene, tetrahydrofuran, o-dichlorobenzene, triethylamine and the like, and mixtures thereof. Currently preferred non-polar aprotic organic solvents include toluene, chlorobenzene, and dichloromethane.

Examples of polar aprotic organic solvents which can be employed in the process of the invention include acetonitrile, sulfolane, pyridine and the like, and mixtures thereof. Currently preferred polar aprotic organic solvents include acetonitrile.

Although not specifically required, it is preferred to utilize the same solvent to carry out both reaction steps, ie for the preparation of the compound of the formula II and then the treatment of the compound of the formula II to obtain the compound of the formula I, in order to avoid additional process equipment for recovering additional solvents.

The amount of solvent utilized in the process of the invention is at least the amount necessary to solubilize the urea.

In the embodiment including the preparation of the tri-substituted urea the amount of a substituted isocyanate reacted with di-substituted amine to produce the tri-substituted urea can be expressed in terms of a ratio. That is, broadly, the ratio of the number of moles of isocyanate reacted with di-substituted amine will be about 1:1 to about 20:1, preferably about 1:1. The tri-substituted urea is the treated with the electrophile or oxophile in an amount sufficient to activate the urea. This activated urea is then reacted with an additional di-substituted amine in an amount expressed as a ratio to be about 1:1 to about 20:1 to yield optimally one mole of the penta-substituted guanidine and one mole of water. The acid conditions of the reaction of activated urea with the amine leads to the formation of the salt of the guanidine. Thus, the presence of a base in this reaction or the addition of a base at the end of the reaction is required to neutralize the salt or to liberate the guanidine at a pH of 12–14 in the aqueous phase of the product. Appropriate bases are NaOH, KOH, LiOH and the like. Neutralization occurs in an exothermic reaction releasing an unprotonated form of the penta-substituted guanidine which is extracted from the aqueous phase by successive washes with an organic solvent, preferably toluene. The organic layers, containing the penta-substituted guanidine, are collected for purification by usual means such as vacuum distillation. The overall yield is in the 90 mole % range recovered penta-substituted guanidine.

Applicable carbonyl activating agents for use in the process of the invention may include phosgene, but preferably include $POX_3$, $PSX_3$, $SOX_2$, $SO_3$, $PX_5$, $P_2O_5$, $NO_y$, $NOX$ and halides or oxyhalides of metals selected from the group consisting of transition metals, Group III B metals, Group IV B metals, and Group V B metals, and mixtures thereof wherein X is chlorine or bromine, halides are chlorides or bromides, and y is 1 or 2. The periodic table nomenclature used herein is that of the International Union of Pure and Applied Chemistry (IUPAC).

Examples of suitable carbonyl activating agents include $POCl_3$, $PCl_3$, trifluoroacetic anhydride, $PBr_3$, $SOCl_2$, $PCl_5$, NO, $NO_2$, NOCl, $AlCl_3$, $VOCl_3$, $AlBr_3$, $TiBr_4$, $BBr_3$ and $TiCl_4$.

The currently preferred carbonyl activating agents are $POCl_3$, $PCl_3$ and $SOCl_2$ because of the extremely high yields achievable with these compounds under mild reaction conditions.

In the activation of the tri-substituted urea in the present invention prior to its reaction with the di-substituted amine, the amount of electrophilic or oxophilic dehydrating agent can be conveniently expressed in terms of a ratio based on the number of equivalents of amine in the di-substituted amine of the reaction. Broadly, the ratio of the number of moles of electrophilic or oxophilic dehydrating agent to the number of equivalents of amine in the di-substituted amine will be about 0.4:1 to about 2:1, preferably about 0.9:1 to about 1.1:1 and most preferably 1:1.

The reaction between the compound of the formula II and formula III is conducted under a nitrogen blanket at atmospheric pressure (0 psig), preferably beginning with dry reactants and reaction conditions.

The compound of formula II is, preferably pretreated with a carbonyl activating agent, preferably $POCl_3$, to form an activated compound of formula II. The carbonyl activating agent is added, preferably in a solvent, preferably toluene, to a solution of the compound of formula II. This addition is preferably conducted in a manner in which exothermic conditions of the reaction are controlled, i.e. the addition is conducted slowly, preferably over a period of about 30 minutes and may be as long as 90 minutes, with good mixing and maintenance of a temperature at about 60° C. Such a metered addition with adequate mixing and temperature control prevents the formation of solids which reduce final product yield. Preferably the reaction mixture following the addition of the electrophile or oxophile should be stirred and maintained at about 60° C. after the addition is complete for about 10 minutes to a total of up to 5 hours to avoid a yield decrease. If it is necessary to keep this mixture for longer than 5 hours the reaction mass should be cooled and maintained at less that 25° C. to avoid degradation of the activated compound of formula II.

The activated compound of formula II is preferably treated with the compound of formula III immediately in view of its limited stability. Its degradation would reduce the yield. The temperature of the reaction mixture of this treatment step is preferably maintained in the range of 20°–30° C. As in the pretreatment of the compound of formula II the addition of the compound of formula III is preferably conducted over a time sufficient for adequate mixing to activate the compound of formula II. Temperature control is also accomplished here as above. For example, in the preparation of cyclohexyltetraethylguanidine an optimal time for such activation of cyclohexyldiethylurea is at least about 36 minutes with adequate mixing to control temperatures of this reaction which is also exothermic. Longer addition times are also acceptable to accomplish an optimum mixing and temperature control for the best yield.

After the addition of the compound of formula III to the activated compound of formula II, water is added all at once or gradually to this reaction mixture at the same time as maintaining a temperature of between about 20° to about 30° C. for this step. Good mixing to ensure contact between the aqueous and organic phases for a time sufficient to transfer the product of the formula I to the aqueous phase. Recovery of the compound of the formula I may be accomplished by any means known. For example, after phase separation the aqueous phase may be washed three times or more with fresh toluene to remove unreacted activated compound of the formula II and other organic byproducts, if present. Preferably each washing should provide a contact time sufficient for removal of undesirable materials. The washing is preferably accomplished with vigorous agitation to ensure good mass transfer between the two phases. The final aqueous phase is expected to have a pH of 6–7 or lower.

After phase separation, a base, preferably NaOH, is added to the reactor, which contains the aqueous phase from the previous extraction, to prevent the formation of solids. Both the addition of water and sodium hydroxide is preferably made with moderate agitation. The sodium hydroxide may be in a 25 % solution and is added all at once or gradually. Again the addition here is accompanied by a slight exotherm. The temperature should be maintained in the range of about 20° to 30° C. Recovery of the compound of the formula I may be accomplished by any conventional means known in the art. For example, extraction of the compound formula III an organic phase is then conducted with an organic solvent, preferably toluene, with stirring and contact time as before. Purification is also accomplished in the usual manner, preferably distillation under a mild vacuum (about 100 Torr) which is gradually further reduced. The temperature and pressure may be adjusted to optimize this vacuum distillation depending upon the physical characteristics of the compound of the formula I, such as boiling point, decomposition temperature and the like.

Initial preparation of the compound of formula II in the invention process is accomplished by addition of a compound of the formula V to a compound of the formula IV in a solvent, preferably toluene, at a temperature which is maintained in the range of about 10° to about 20° C. for a period of at least 10 minutes for best results. Good mixing and metered addition of the compound of formula V and avoidance of undesired temperature increase due to the exothermic nature of the reaction is preferred. However, following the addition of the compound of formula V the temperature may be raised to about 60° C. for about 30 minutes to ensure completion of the reaction. If this operating temperature of the reaction to completion is above the temperature of the compound of the formula II, then sufficient cooling must be provided in a reflux condenser to avoid the loss of desired product of this preparation in vapors.

All reaction steps for obtaining the product of the formula I may be performed without separation. All reaction steps may be performed in one reaction vessel such as in a batch-wise or semi-batch-wise process or could also be in a continuous process.

Contemplated equivalence of the general formulas set forth above for each of the compounds of the formula II, III, IV and V are compounds otherwise corresponding thereto and having the same general properties wherein one or more of the various R groups are simple variations of the substituents as defined therein.

In addition, where a substituent is designated as, or can be a hydrogen, the exact chemical nature of a substituent which is other than hydrogen at that position is not critical so long as it does not adversely effect the overall synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials. An example of known isocyanates and/or a process to prepare such isocyanates is found in U.S. Pat. No. 5,189,205.

The invention will now be further disclosed in the following illustrative examples wherein parts and percentages are given on a molar basis unless otherwise specified.

EXAMPLES

Preparation 1

Cyclohexyl-diethylurea

Cyclohexyl isocyanate (250 g, 2.0 mol) is added dropwise over a 30 min period to a mixed hexanes (1200 ml) solution of diethylamine (160 g, 2.2 mol) in a three neck round bottomed flask. After the reaction is refluxed at 70° C. for 2 hours the hot solution is poured into a beaker. Crystals formed upon standing at room temperature overnight. The product is collected by filtration and the mother liquor is cooled in an ice-water bath upon which more urea is crystallized out. After air drying 386 g (98%) cyclohexyl-diethylurea is obtained. $^1$H NMR (CDCl$_3$) δ 4.12–4.23 (b, 1H), 3.59–3.72 (m, 1H), 3.25 (q, 4H), 1.13 (t, 6H) ppm.

Preparation 2

Cyclohexyl-diisopropylurea

Cyclohexylisocyanate (125 g, 1.0 mol) is added dropwise over a 30 min period to a mixed hexanes (1500 ml) solution of diisopropylamine (122 g, 1.2 mol) in a three neck round bottomed flask. After the reaction is refluxed at 70° C. for 2 hours the hot solution is poured into a beaker. Precipitate formed upon standing at room temperature overnight. The product is collected by filtration and the mother liquor is cooled in an ice-water bath upon which more urea is precipitated out. After air drying 226 g (100%) cyclohexyl-diisopropylurea is obtained. $^1$H NMR (CDCl$_3$) δ 4.03–4.11 (b, 1H), 3.88 (m, 2H), 3.69 (m, 1H), 1.12–2.0 (m, 10H), 1.22 (d, 12H) ppm.

Preparation 3

Cyclohexyl-di-n-propylurea

Cyclohexyl isocyanate (125 g, 1.0 mol) is added dropwise over a 30 min period to a mixed hexanes (1100 ml) solution of di-n-propylamine (116 g, 1.15 mol) in a three neck round bottomed flask. After the reaction is refluxed at 70° C. for 2 hours the hot solution is poured into a beaker. Precipitate formed upon standing at room temperature overnight. The product is collected by filtration and the mother liquor is cooled in an ice-water bath upon which more urea is precipitated out. After air drying 212 g (94%) cyclohexyl-dipropylurea is obtained. $^1$H NMR (CDCl$_3$) δ 4.09 (d, 1H), 3.62 (m,1H), 3.10 (t, 4H), 1.02–1.96 (m, 10H), 1.53 (q, 4H), 0.88 (t, 6H) ppm.

Example 1

Cyclohexyl-tetraethylguanidine

Phosphorus oxychloride (144 ml, 237 g, 1.55 mol) is added dropwise over a 1.5 hour period to a toluene (800 ml) solution of cyclohexyl-diethylurea (297 g, 1.5 mol). The reaction is stirred overnight at room temperature. Diethylamine (330 ml, 234 g, 3.2 mol) is added dropwise for over a 2 hour period, then stirred 3 hours at room temperature. The reaction mixture is poured into water (3000 ml). The water layer is extracted with toluene (3×200 ml). The organic layer and extracts are combined and dried over Na$_2$CO$_3$, filtered and concentrated. The residue is further distilled under vacuum (ca. 0.3–0.5 torr) collecting product, cyclohexyl-tetraethylguanidine, at 110°–112° C. (334 g, 88%) of 99% purity as judged by gas chromatography. $^1$H NMR (CD$_3$CN) δ 3.13–3.23 (m, 1H), 3.07 (q, 4H), 2.97 (q, 4H), 1.13–1.77 (m, 10H), 1.0 (t, 6H), 0.98 (t, 6H) ppm.

Example 2

Cyclohexyl-diethyl-diisopropylguanidine

Phosphorus oxychloride (78.2 g, 0.51 mol) is added dropwise over 1 hour period to a toluene (250 ml) solution of cyclohexyl-diethylurea (99 g, 0.5 mol). The reaction is stirred overnight at room temperature. Diisopropylamine (101 g, 1.0 mol). is added dropwise for over a 1 hour period, then stirred 2 hours at room temperature. The reaction mixture is poured into water (300 ml). The water layer is extracted with toluene (3×100 ml) and the toluene layers are discarded. Sodium hydroxide (120 g, 3 mol) is slowly added to the aqueous layer in an ice-water bath. Two layers formed and the aqueous layer is extracted with diethylether (2×100 ml). The organic layer and extracts are combined and dried over $Na_2CO_3$, filtered and concentrated. The residue is further distilled under vacuum (ca, 0.3–0.5 torr) collecting product, cyclohexyl-diethyl-diisopropylguanidine, at 137°–140° C. (95 g, 68%) of 99% purity as judged by gas chromatography. $^1H$ NMR ($CDCl_3$) δ 3.57 (m, 1H), 3.36 (m, 1H), 3.21 (q, 2H), 2.94 (q, 2H, 3.12 (m, 1H0, 2.93 (q, 2H), 1.13–1.77 (m, 10H), 1.20 (d, 6H), 1.12(d, 6H), 1.00 (t, 3H), 0.99 (t, 3H) ppm.

Example 3

Cyclohexyl-tetraisopropylguanidine

Phosphorus oxychloride (96 ml, 1.03 mol) is added dropwise over 30 min period to a toluene (800 ml) solution of cyclohexyl-diisopropylurea (226 g, 1.0 mol). The reaction is stirred 3.5 hours at 50° C., then stirred overnight at room temperature. Diisopropylamine (310 ml, 2.18 mol) is added to the reaction mixture dropwise for over a 2 hour period, then stirred 2 hours at room temperature. The reaction mixture is poured into water (2000 ml). The water layer is extracted with toluene (3×150 ml) and the toluene layer is discarded. Sodium hydroxide (240 g, 6 mol) is slowly added to the aqueous layer in an ice-water bath. Two layers formed and the aqueous layer is extracted with diethylether (2×150 ml). The organic layer and the extracts are combined and dried over $Na_2CO_3$, filtered and concentrated. The residue is further distilled under vacuum (ca. 0.3–0.5 torr) collecting product, cyclohexyl-tetraisopropylguanidine, at 140°–143° C. (250g, 80%) of 99% purity as judged by gas chromatography. $^1H$ NMR ($CDCl_3$) δ 3.75–3.9(m, 1H), 3.37(m, 1H), 3.22–3.31 (m,1H), 1.12–1.77 (m, 10H), 1.22 (d, 6H), 1.14 (d, 6H) ppm.

Example 4

Cyclohexyl-tetrapropylguanidine

Phosphorus oxychloride (86 ml, 142 g, 0.92 mol) is added dropwise over a 1 hour period to a toluene (800 ml) solution of cyclohexyl-dipropylurea (191 g, 0.845 mol). The reaction is stirred overnight at room temperature. Dipropylamine (221 g, 300 ml, 2.19) is added dropwise for over a 2 hour period, then stirred 2 hours at room temperature. Sodium hydroxide solution (6×0.92 mol NaOH and 500 ml water) is slowly added to the reaction mixture in an ice-water bath. The water layer is extracted with diethylether (3×100 ml). The organic layers are combined and dried over $Na_2CO_3$, filtered and concentrated. The residue is further distilled under vacuum (ca. 0.3–0.5 torr) collecting product, cyclohexyl-tetrapropylguanidine, at 150° C. (235 g, 90%) of 99% purity as judged by gas chromatography. $^1H$ NMR ($CDCl_3$) δ 3.10 (m, 1H), 3.02 (b, 4H), 2.88 (t, 4H, 1.77–1.12 (m, 10H), 1.42 (q, 8H), 0.82 (t, 6H), 0.80 (t, 6H) ppm.

Example 5

Cyclohexyltetraethylguanidine

Cyclohexylisocyanate (13.4 lb., 48.6 mol) is charged to a 100-gallon glass-lined reactor. The reactor is blanketed with nitrogen and charged with toluene (185.9 lb.). The reaction mass is agitated and cooled to 15°–20° C. Diethylamine (7.9 lb, 49.1 mol) is charged to the reactor, with agitation, over a period of 15 minutes. The temperature of the reaction mass is held under 20° C. during the addition of diethylamine. The temperature of the reaction mass is then increased to 60° C. and maintained at 60° C. for 30 minutes.

A solution of phosphorous oxychloride (19.7 lb., 58.3 mol) in toluene (92.9 lb) is added to the reactor, with agitation, over a period of 40 minutes. The temperature of the reaction mass is maintained at 55°–65° C. during the addition of the phosphorous oxychloride solution. The reaction mass is held at 55°–60° C. for 10 minutes after the addition is complete. The reaction mass is then cooled to 20° C.

Diethylamine (43.4 lb., 269.2 mol) is added to the reactor over a period of 40 minutes. The temperature of the reaction mass is held below 35° C. during the addition. The reaction mass is maintained at 25°–30° C. for 20 minutes after the addition of diethylamine is complete. The reaction mass is then cooled to 20° C.

Deionized water (232.5 lb) is added to the reaction mass, with vigorous agitation, over a period of 20 minutes. The temperature of the reaction mass is maintained at 15°–20° C. during the addition of the water. The mass is agitated for 15 minutes and then allowed to settle for 20 minutes. The aqueous and organic phases are separated and removed from the reactor. The organic phase is returned to the reactor and washed again with additional deionized water (232.5 lb). This wash cycle is repeated a total of three times.

The combined aqueous phases from the wash step contain cyclohexyl tetraethyl guanidine hydrochloride. These are combined in the reactor and an additional 200 lb of deionized water is added to the mass. A 25% solution of sodium hydroxide (123.5 lb.) is added to the mass, with agitation. The temperature is maintained below 30° C.

Toluene (58.1 lb.) is added to the mass with vigorous agitation. The mass is agitated for 15 minutes and then allowed to settle for 20 minutes. The aqueous phase and organic phase are separated and removed from the reactor. The aqueous phase is returned to the reactor and the organic phase is retained for distillation. The aqueous phase is washed with an additional 58.1 lb. of toluene. The wash cycle is repeated a total of three times. The organic phase contains cyclohexyl tetraethyl guanidine.

The combined organic phases from the extraction step are combined in a high-vacuum-m still. The still pressure is reduced to approximately 100 mm Hg and the still temperature increased until boil up is attained. The toluene is distilled from the still pot. The pressure is then reduced to less than 1 mm Hg and the temperature further increased in order to distill the cyclohexyl tetraethyl guanidine. The material distills at approximately 85° C. at 0.5 mm Hg. Cyclohexyl tetraethyl guanidine (25.4 lb., 45.5 mol) distillate is collected, for a recovered yield of 93%.

That which is claimed is:

1. A process for preparing a penta-substituted guanidine which comprises treating a tri-substituted urea with a di-substituted amine in the presence of an aprotic solvent, a base, and an activating agent which is a carbonyl activating agent under conditions of time and temperature sufficient to produce the corresponding guanidines.

2. A process according to claim 1 wherein the tri-substituted urea is prepared by a process which comprises contacting equimolar amounts of a substituted isocyanate and a di-substituted amine also in the presence of an aprotic solvent and under conditions of time and temperature sufficient to produce the corresponding tri-substituted ureas, or treating a urea with a primary amines to produce the corresponding tri-substituted ureas.

3. A process for preparing a penta-substituted guanidine of the formula (I)

$$R_2R_3N-\underset{\underset{R_1}{\overset{\displaystyle N}{\|}}}{C}-NR_4R_5 \qquad I$$

wherein $R_1$, $R_2$, $R_3$, $R_4$ and $R_5$ are the same or different and are selected from the group consisting of alkyl, cycloalkyl, aryl, alkaryl, aralkyl, alkenyl, cycloalkenyl, alkenaryl and aralkenyl;

which comprises treating a compound of the formula (II)

$$R_1NH-\underset{\underset{\displaystyle}{\overset{\displaystyle O}{\|}}}{C}-NR_2R_3 \qquad II$$

with a compound of the formula (III)

$$R_4R_5NH \qquad III$$

in an aprotic organic solvent in the presence of an activating agent which is a carbonyl activating agent to obtain the acid addition salt of the compound of formula I, optionally in the presence of a base such that the pH of the product mixture is about the same as or higher than the product of the formula I or followed by the addition of a base to free the salt under reaction conditions of time and temperature sufficient to produce the corresponding guanidine; and further optionally, wherein the compound of the formula II is prepared by a process which comprises
(1) treating a compound of the formula (IV)

$$R_1NCO \qquad IV$$

with a compound of the formula (V)

$$R_2R_3NH \qquad V$$

wherein $R_1$, $R_2$ and $R_3$ are as defined above;
or
(2) treating a compound of the formula (VI)

$$NH_2C(O)NH_2 \qquad VI$$

with a compound of the formula (VII)

$$R_1NH_2 \qquad VII$$

and then with a compound of the formula (V)

$$R_2R_3NH \qquad V$$

or
(2) treating a compound of the formula (VI)

$$NH_2C(O)NH_2 \qquad VI$$

with a compound of the formula (V)

$$R_2R_3NH \qquad V$$

and then with a compound of the formula (VII)

$$R_1NH_2; \qquad VII$$

to obtain a compound of the formula II.

4. A process of claim 3 wherein the compound of the formula II is prepared by a process
which comprises
treating a compound of the formula (IV)

$$R_1NCO \qquad IV$$

with a compound of the formula (V)

$$R_2R_3NH \qquad V$$

wherein $R_1$, $R_2$ and $R_3$ are as defined above.

5. A process of claim 3 wherein the compound of the formula II is prepared by a process which comprises treating a compound of the formula (VI)

$$NH_2C(O)NH_2 \qquad VI$$

with a compound of the formula (VII)

$$R_1NH_2 \qquad VII$$

and then with a compound of the formula (V)

$$R_2R_3NH \qquad V$$

or
treating a compound of the formula (VI)

$$NH_2C(O)NH_2 \qquad VI$$

with a compound of the formula (V)

$$R_2R_3NH \qquad V$$

and then with a compound of the formula (VII)

$$R_1NH_2. \qquad VII$$

6. A process of claim 3 wherein the carbonyl activating agent is selected from the group consisting of $POX_3$, $PX_3$, $SOX_2$, $SO_2X_2$, $SO_3$, $PX_5$, $P_2O_5$, $NO_y$, NOX and halides or oxyhalides of metals selected from the group consisting of transition metals, Group III B metals, Group IV B metals, and Group V B metals, and mixtures thereof wherein X is chlorine or bromine, halides are chlorides or bromides, and y is 1 or 2.

7. The process according to claim 3 wherein said aprotic organic solvent is selected from the group consisting of dichloromethane, tetrahydrofuran, acetonitrile, o-dichloromethane, toluene, and pyridine.

8. The process according to claim 3 wherein the base is selected from the group consisting of NaOH, KOH and LiOH.

9. The process according to claim 1 wherein said carbonyl activating agent is selected from the group consisting of $POCl_3$, $SOCl_2$, $SO_2Cl_2$, $SO_3$, $PCl_3$, trifluoroacetic anhydride, $TiBr_4$, $AlCl_3$, $VOCl_3$ and $BBr_3$.

10. The process according to claim 3 for preparing a penta-substituted guanidine which is cyclohexyl tetraethyl guanidine which comprises treating cyclohexylisocyanate in toluene with from a four to six molar excess of diethylamine and from a one to two molar excess of $POCl_3$ to obtain cyclohexyltetraethyl guanidine hydrochloride which is then treated with NaOH to obtain cyclohexyl tetraethyl guanidine.

* * * * *

UNITED STATES PATENT AND TRADEMARK OFFICE
CERTIFICATE OF CORRECTION

PATENT NO. : 5,696,290

DATED : December 9, 1997

INVENTOR(S) : Kenneth W. Ruettimann, William D. McGhee, A. John Solodar

It is certified that error appears in the above-identified patent and that said Letters Patent are hereby corrected as shown below:

Column 1, line 51, the term "Orgsnischen" should be "Organischen"
Column 2, line 35, the term "Iabilie" should be "labile"
Column 4, line 45, the term "hoax" should be "non"
Column 8, line 13, the term "Cyclohexyl-diisopropylarea" should be "Cyclohexyl-diisopropylurea"
Column 10, line 44, the term "high-vacuum-m" should be "high-vacuum"

Signed and Sealed this

Fifteenth Day of May, 2001

Attest:

NICHOLAS P. GODICI

Attesting Officer     Acting Director of the United States Patent and Trademark Office